United States Patent
Åkerfeldt et al.

[11] Patent Number: 5,868,684
[45] Date of Patent: Feb. 9, 1999

[54] DEVICE FOR HARD TISSUE BIOPSY SAMPLING

[75] Inventors: Dan Åkerfeldt; Gunnar Åstroem; Håkan Ahlstroem, all of Upsala, Sweden

[73] Assignee: Radi Medical Systems AB, Upsala, Sweden

[21] Appl. No.: 663,123

[22] PCT Filed: Dec. 22, 1994

[86] PCT No.: PCT/SE94/01244

§ 371 Date: Jun. 21, 1996

§ 102(e) Date: Jun. 21, 1996

[87] PCT Pub. No.: WO95/17126

PCT Pub. Date: Jun. 29, 1995

[30] Foreign Application Priority Data

Dec. 22, 1993 [SE] Sweden ................................. 9304261

[51] Int. Cl.$^6$ ................................................. A61B 10/00
[52] U.S. Cl. ..................... 600/564; 600/567; 604/264; 604/164; 606/185
[58] Field of Search ..................... 128/749, 751, 128/753, 754, 757; 606/167, 184, 185; 604/165, 164, 264; 600/564, 567, 570

[56] References Cited

U.S. PATENT DOCUMENTS

| | | | |
|---|---|---|---|
| Re. 35,459 | 2/1997 | Jonkman | 604/165 |
| 1,626,839 | 5/1927 | Kallmeyer | 604/264 |
| 2,516,492 | 2/1950 | Turkel | 128/751 |
| 3,628,524 | 12/1971 | Jamshidi | 128/2 B |
| 3,630,192 | 12/1971 | Jamshidi . | |
| 3,850,158 | 11/1974 | Elias et al. . | |
| 4,258,722 | 3/1981 | Sessions et al. | 128/753 |
| 4,306,570 | 12/1981 | Matthews | 128/754 |
| 4,368,730 | 1/1983 | Sharrock | 604/164 |
| 4,487,209 | 12/1984 | Mehl | 128/754 |
| 4,543,966 | 10/1985 | Islam et al. | 128/754 |
| 4,643,196 | 2/1987 | Tanaka et al. | 128/753 |
| 5,111,828 | 5/1992 | Kornberg et al. | 600/564 |
| 5,122,134 | 6/1992 | Borzone et al. | 506/80 |
| 5,234,455 | 8/1993 | Mulbollan | 606/191 |
| 5,269,316 | 12/1993 | Spitalny | 128/754 |
| 5,401,248 | 3/1995 | Bencini | 604/264 |
| 5,423,824 | 6/1995 | Akerfeldt et al. | 606/80 |
| 5,578,006 | 11/1996 | Schon | 604/264 |
| 5,595,186 | 1/1997 | Rubinstein et al. | 128/751 |
| 5,676,682 | 10/1997 | Yoon | 604/264 |

FOREIGN PATENT DOCUMENTS

| | | |
|---|---|---|
| 0 296 421 | 12/1988 | European Pat. Off. . |
| 0 427 367 | 5/1991 | European Pat. Off. . |
| 470 177 | 11/1993 | Sweden . |
| 2171537 | 8/1986 | United Kingdom . |

*Primary Examiner*—Richard J. Apley
*Assistant Examiner*—Justine R. Yu
*Attorney, Agent, or Firm*—Foley & Lardner

[57] ABSTRACT

The invention relates to a hard tissue biopsy sampling device, e.g. for bone in humans or animals, comprising a tube shaped casing or sleeve with a distal end provided with a cutting edge and a proximal end. The invention further comprises a needle insertable in the sleeve, the needle extending out of the distal end of the sleeve, and having a tip allowing penetration in the hard tissue. The sleeve exhibits in the vicinity of its distal end a portion having reduced outer diameter. The distal end has a section with reducing diameter, such that the inner diameter of the interior of the device is continuously reduced over at least the major part of the section. In side projection, the cutting edge forms an angle in relation to a perpendicular plane through the cross-section of the device, the angle preferably being 17°–23°.

20 Claims, 2 Drawing Sheets

DEVICE FOR HARD TISSUE BIOPSY SAMPLING

FIELD OF THE INVENTION

The present invention relates to biopsy sampling and in particular to a device for such sampling in hard tissue on e.g. humans or animals.

BACKGROUND OF THE INVENTION

The skeleton is the site for a number of different pathological lesions, e.g. primary and secondary malign tumours, benign tumours, infectious lesions, blood diseases etc. The lesions are often visible on X-ray pictures of the skeleton, but mostly it is not possible to asses the cause of the lesion by means of such X-ray pictures. In order to determine the nature of the lesion with certainty, portions of the bone must be taken out and examined under microscope.

Biopsy sampling in bone is difficult to carry out with the aid of a biopsy needle because the lesion often is delimited by the hard surface layer of the bone, i.e. cortical bone tissue.

Today essentially two methods are in use for taking biopsy samples from bone, namely operative biopsy and percutaneous needle biopsy. An operative ingress in most cases yields a good result, but frequently requires full narcosis, and in addition it is resource demanding and costly. Percutaneous needle biopsy is performed under local anesthesia, and the needle consists commonly of a sampling tube that is either provided with saw-teeth or is highly sharpened, and which is passed through the lesion, whereby a biopsy sample is cut or "punched" out. During insertion a stylet or needle (for the purposes of this application "stylet" and "needle" are regarded as synonymous) is placed in the tube, thereby creating a sharp distal tip of the tube for making the insertion through the softer parts easier. Examples of such needles are disclosed in EP-0 296 421 (the Ostycut needle) and in U.S. Pat No. 3,628,524 (the Jamshidi needle). These documents are incorporated herein by reference.

Existing biopsy needles have the considerable disadvantage that they may not be easily inserted into the bone because of friction between needle and bone. Biopsy needles such as Jamshidi or Ostycut all have a needle tip that can only penetrate thin or soft cortical bone due to the tip not cutting away material like a drill, but instead are to wedge there way in with great feeding force in combination with rotation.

Another disadvantage is that the large friction occurring between needle and cortical bone, makes the manipulation of the needle towards the target difficult, and causes development of heat which the patient may experience as painful. There are also needle types where the distal end of the needle has saw-tooth-shaped teeth. An example of such a needle is disclosed in U.S. Pat. No. 4,306,570 (the Corb needle). However, the drawbacks with saw teeth are that the teeth become clogged by drilling chips when drilling deeper than the height of the teeth. Furthermore the saw teeth must be protected by an outer protective tube during insertion through the soft portions of the body, in order not to cause damage, and this increases the required outer diameter of the needle.

In U.S. Pat. No. 4,543,966 there is disclosed a needle having a tip wherein the inner diameter of the tip is smaller than the inner diameter of the major part of the needle interior. The portion with reduced inner diameter at the tip has a longitudinal extension of 0.5–10 mm. The provision of such reduced inner diameter in the form of a cylindrical front end portion, is said to increase the amount of tissue sample that may be taken out, and also that the outer regions of the sample remains undamaged.

However, the cylindrical portion with reduced diameter causes some problem in that there may occur a stoppage or "jamming" of tissue at the intake opening, because of the friction in the narrow cylindrical portion.

SUMMARY OF THE INVENTION

The present invention, as defined in the attached claims, overcomes the above described disadvantages present in known bone biopsy needles by providing a biopsy sampling device for penetration of hard tissue. It comprises a tube shaped casing or sleeve with a distal and a proximal end. A needle is insertable in the sleeve, said needle extending out of the distal end of the sleeve. The needle has a tip allowing penetration in said hard tissue, and the sleeve exhibits a portion having reduced outer diameter at its distal end.

Preferably also the tip portion of the sleeve is provided with a reduced diameter. Thereby the tissue sample, after having been cut, easily "flows" into the needle interior by virtue of the interior volume of the needle expanding immediately inside the cutting edge at the tip.

BRIEF DESCRIPTION OF THE DRAWINGS

The invention will now be described in detail with reference to the attached drawings, wherein.

DETAILED DESCRIPTION OF PREFERRED EMBODIMENTS

Figure 5:
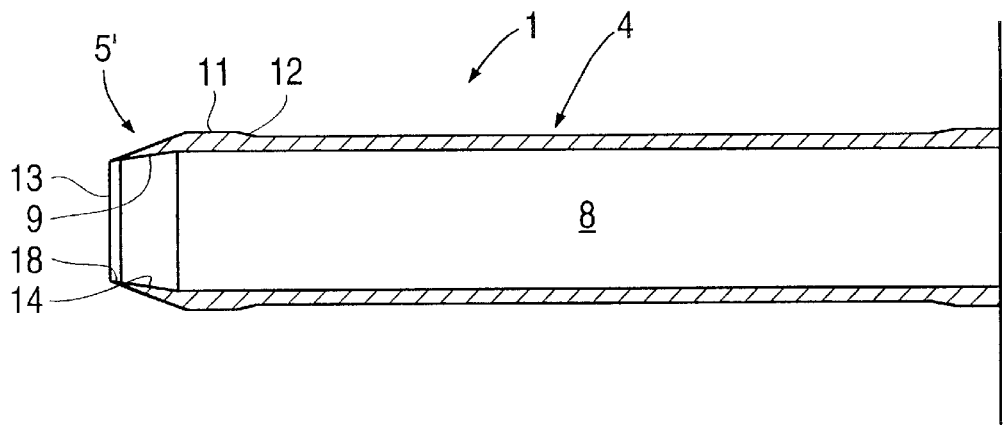
FIG. 5 is a longitudinal cross section of a distal part of a first embodiment of the sleeve.

Like elements will be designated with the same reference numerals throughout the description and Figures.

Figure 1A:
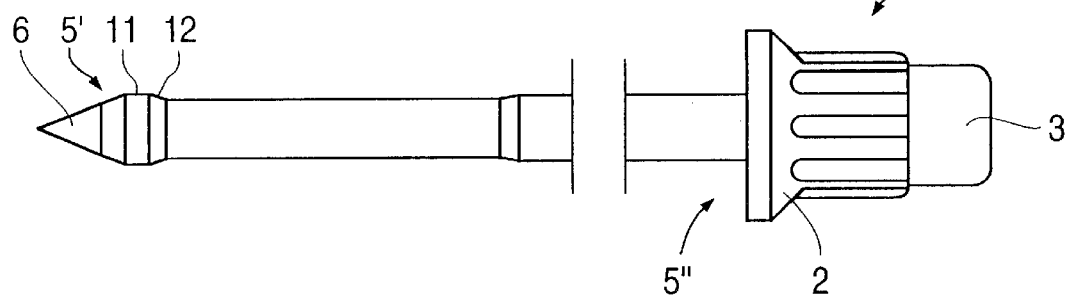
FIG. 1a is a schematic longitudinal view of the device according to a first embodiment of the invention with a needle inserted in the sleeve.
Figure 3:
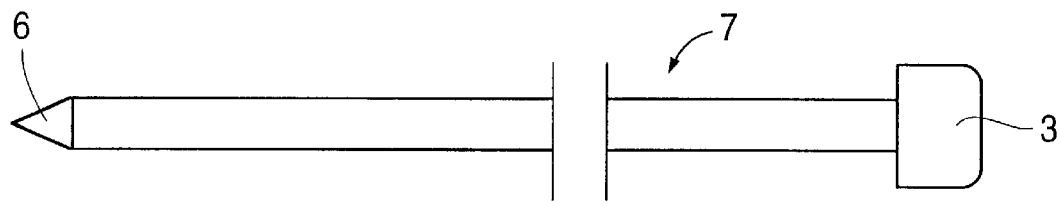
FIG. 3 is a view of the inner needle.
Figure 2B:
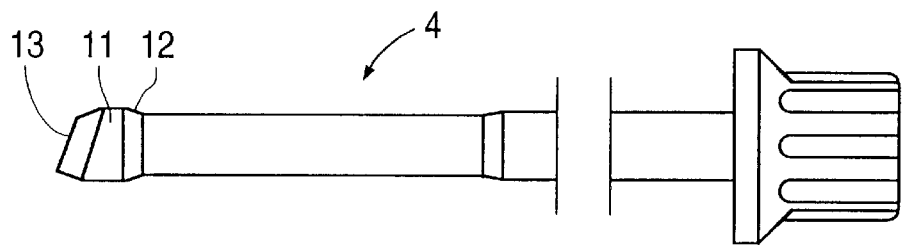
FIG. 2b is a view of only the sleeve according to the second embodiment.
Figure 1B:
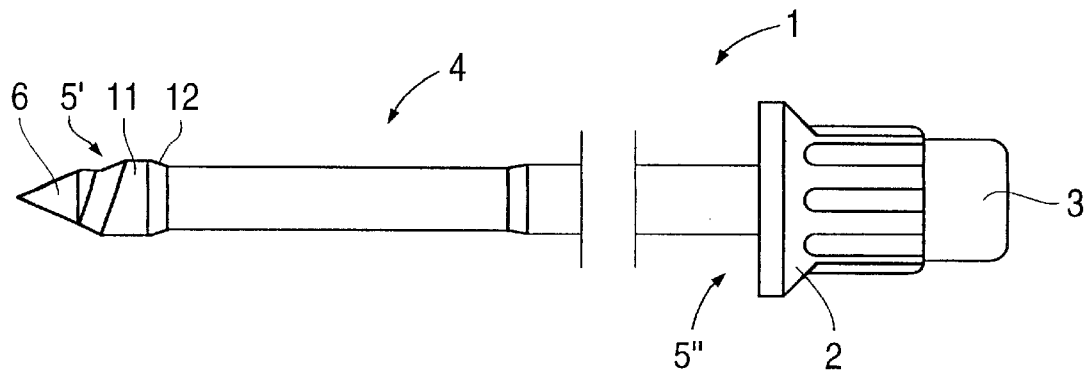
FIG. 1b is a schematic longitudinal view of the device according to a second embodiment of the invention with a needle inserted in the sleeve.

The biopsy needle assembly of the invention, two different embodiments of which is shown in FIGS. 1a and 1b respectively, comprises a sleeve generally designated with numeral 1, the distal end 5' of which is externally cone shaped or bevelled. Around the proximal end 5" of the sleeve a handle 2 is attached. In the tube a movable, massive needle 7 (FIG. 3) is inserted. Around the proximal end of the needle a handle 3 is attached.

In FIG. 1a, the distal end 5' of the sleeve 1 is bevelled, forming a truncated cone portion, and the tip 6 of the needle 7 extending out of the sleeve is also bevelled at essentially the same angle, such that there is formed a penetrating tip 5', 6 on the device as a whole. Between the truncated cone portion and the portion with reduced diameter 4, there is a ring shaped portion 11 having the same diameter as the nominal diameter N of the sleeve. The ring shaped portion 11 merges into the reduced diameter portion 4 via a bevelled portion 12. The bevel angle of bevelled portion 12 may be 0.1°–80°. It is preferable that the bevel angle be 1°–60°, and more preferably be 5°–45°.

Figure 2A:
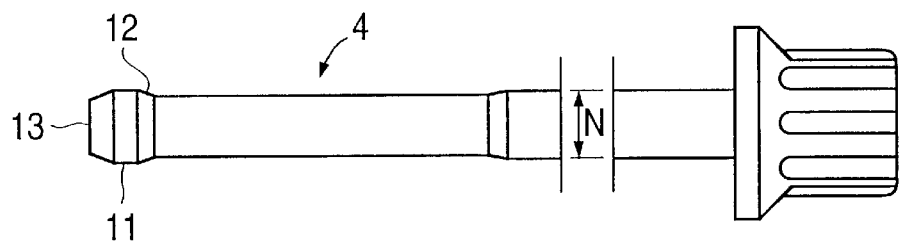
FIG. 2a is a view of only the sleeve according to the first embodiment.

The sleeve 1 in a first embodiment, shown in FIG. 2a, has a portion 4 with reduced diameter, and having a longitudinal extension from in the vicinity of the distal end over a distance towards the proximal end, whereby the length of the portion 4 corresponds to at least 10%, preferably about 15–75% of the length of the sleeve.

The thickness of the material in the portion 4 with reduced diameter is about 50–90% of the nominal thickness of the sleeve.

Figure 4:
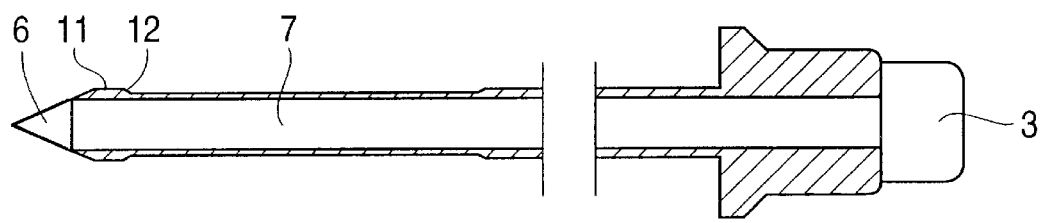
FIG. 4 is a longitudinal cross section of the sleeve, with an inserted needle not in section.

In FIG. 4 there is shown a section of the embodiment of FIG. 1a, shown with a solid needle 7 in place. In this embodiment the sleeve 1 has a uniform inner diameter along its entire length.

Figure 6:
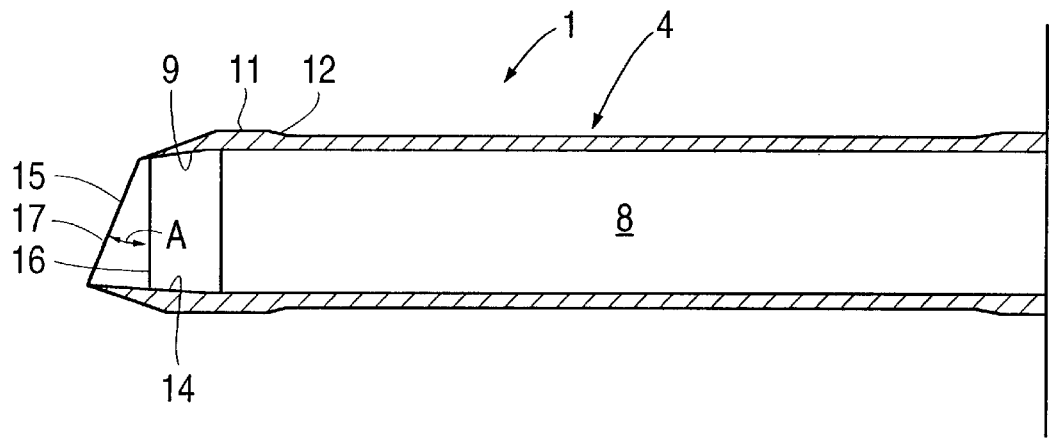
FIG. 6 is a cross sectional view of a distal part of a preferred embodiment of the sleeve.

Turning now to FIG. 5 there is shown the distal part of another embodiment of the sleeve, designated with numeral 1. The distal end portion 5' of said sleeve is designed exteriorly much the same as the embodiment shown in FIG. 2a. However, it is modified interiorly in that the major lumen 8 of the sleeve, in the embodiment shown in FIG. 5, has a uniform diameter over practically the entire length of the sleeve 1, but the distal portion 9 of said lumen 8 has a reducing diameter. In contrast, the embodiment of FIG. 4 has a constant inner diameter over its entire lumen 8. The reduction in diameter with respect to the inner lumen 8, as shown in FIGS. 5 and 6, is achieved by mechanically working the distal end of a sleeve "blank", i.e. a tube of steel. This can be done by e.g. placing a rod inside the sleeve blank, said rod having a diameter corresponding to the diameter of the reduction at the distal end. Then said sleeve distal end is exposed to a pressure force by suitable means such that the material essentially plastically flows to adapt to said rod. It is also conceivable to insert a rod having the same diameter as the inner lumen 8 over the major part of its length, and having a reduced diameter tip, with a portion between the two diameters in the shape of a truncated cone, joining said cylindrical portions, such that the rod conforms entirely to the desired inner profile of the lumen. Then the sleeve is exposed to a compressive force such that the sleeve is deformed to conform to the shape of the rod thereby creating the inner profile according to FIG. 5. After compression, the distal end 5', 5" must be sharpened to create a cutting edge 13. This is preferably achieved in a computer controlled robot system in order to achieve high precision. Thereby material is removed such that the outer bevelled surface 5' has a steeper angle than the inner surface 14 at the distal end. It is important to leave a small ring shaped portion 18 having said reduced diameter mentioned above, at the end, otherwise it would be difficult to control the thickness and circumferential contour of the edge 13.

In a specific example that actually has been produced, the length of a sleeve is 158 mm, and the length of the portion with reduced outer diameter is 35 mm. The nominal outer diameter of the sleeve is 1.7 mm, the nominal inner diameter is 1.4 mm, and the outer diameter of the reduced portion is 1.66 mm. The nominal material thickness of the sleeve is 0.15 mm and the material thickness of the reduced portion is thus 0.13 mm. The angle of the bevelled outer end surface 5' is suitably 20° but may vary from 17° to 23°. The bevel angle of the inner surface 14 is not critical but may e.g. amount to 3°–8°.

The sleeve 1 is preferably made of stainless steel, such as SS 2333. During said working process the metal sleeve may be heated to increase plasticity of the material.

In FIG. 6 there is shown a distal part of a preferred embodiment of the sleeve 1. In this embodiment the initial working of the sleeve 1 is identical to the embodiment of FIG. 5, that is the same deformation of the distal end 5' is performed. However, after such initial working the end portion 5' is first machined at an angle deviating from the vertical for creating an angled cutting edge 15. In a preferred form the angle A is 17°–23° with respect to a vertical plane. Then the material at the end portion 5' is removed by grinding such that the bevel angle is the same around the circumference of the end, e.g. 17°–23° (i.e. the cone angle of the truncated cone thus formed). It is nevertheless conceivable to have angles A in a wider range, e.g. 5°–45°, and thus the numeric values indicated above are not limiting.

In this embodiment, the ring shaped portion 15 in FIG. 6 corresponds to the envelope surface of a cylinder having a circular base 16 and an ellipsoid surface 17 of section at the opposite end.

When the device is used, the needle is inserted into the sleeve and the entire assembly is pressed into the tissue. By virtue of the portion having reduced diameter the friction against the tissue when the needle assembly successively is brought into the tissue becomes smaller, in comparison with known needles not having a corresponding reduction. The tissue that has been radially compressed because of the puncture is given the room to expand in the space created by the diameter reduction, and thereby the friction is reduced.

The invention is applicable to most available conventional needles for biopsy sampling.

We claim:

1. A hard tissue biopsy sampling device, suitable for bone in humans or animals, comprising:

a tube shaped sleeve having a nominal outer diameter, the sleeve comprising a distal end and a proximal end;

a needle insertable in the sleeve, the needle extending out of the distal end of the sleeve when inserted in the sleeve, and having a tip enabling penetration in the hard tissue;

the distal end comprising a truncated cone portion ending in a cutting edge, and a ring shaped portion connected to the truncated cone portion and having the same diameter as the nominal outer diameter of the sleeve; and the sleeve comprising a portion having a reduced outer diameter and extending generally between the ring shape portion of the distal end and the proximal end of the sleeve.

2. The device as claimed in claim 1, wherein the sleeve has a material thickness in the portion having reduced outer diameter corresponding to 50–90% of the material thickness of the rest of the sleeve.

3. The device as claimed in claim 1, wherein the distal end is shaped as a truncated cone having a material thickness decreasing toward the distal end and where a base of the truncated cone oriented toward the proximal end, merges into the ring shaped portion which has the same outer diameter as the nominal outer diameter of the sleeve, and which has a small extension in the longitudinal direction of the sleeve.

4. The device as claimed in claim 3, wherein the ring shaped portion merges into the portion having the reduced diameter via a bevelled portion.

5. The device as claimed in claim 4, wherein the bevelled portion having a bevel angle of 0.1°–80°.

6. The device as claimed in claim 5, wherein the bevelled portion has a bevel angle of 1°–60°.

7. The device as claimed in claim 6, wherein the bevelled portion has a bevel angle of 5°–45°.

8. The device as claimed in claim 1, wherein the portion having the reduced outer diameter extends in the longitudinal direction over a distance corresponding to 15–75% of a length of the sleeve.

9. The device as claimed in claim 1, wherein the sleeve comprises a cutting edge lying in a plane which forms an acute angle in relation to a perpendicular plane through a cross section of the device.

10. An essentially tube shaped sleeve adaptable for use together with a needle or stylet, the sleeve having a distal end and a proximal end, said sleeve in a vicinity of its distal end having a reduced outer diameter portion interposed between the distal end and the proximal end, and said sleeve comprising at the distal end thereof a cone shaped section with reducing diameter, such that an inner diameter of an interior of the sleeve is continuously reduced over at least the major part of the cone shaped section, wherein the distal end has a cutting edge which has an ellipsoid shape lying in a plane at an acute angle in relation to a perpendicular plane through the cross section of the sleeve.

11. The sleeve as claimed in claim 10, wherein the portion having reduced outer diameter has a longitudinal extension corresponding to at least 10% of the length of the sleeve.

12. The sleeve as claimed in claim 11, wherein the portion having reduced outer diameter has a longitudinal extension corresponding to 15–75% of the length of the sleeve.

13. The sleeve as claimed in claim 10, comprising an essentially ring shaped portion at the distal end having the same outer diameter as a nominal diameter of the sleeve, whereby the essentially ring shaped portion merges into the portion having reduced diameter via a bevelled portion.

14. The sleeve as claimed in claim 13, wherein the bevelled portion has a bevel angle of 0.1°–80°.

15. The device as claimed in claim 14, wherein the bevelled portion has a bevel angle of 1°–60°.

16. The device as claimed in claim 15, wherein the bevelled portion has a bevel angle of 5°–45°.

17. The sleeve as claimed in claim 8, wherein said angle preferably is 5°–45°.

18. The sleeve as claimed in claim 17, wherein the bevel angle preferably is 17°–23°.

19. A hard tissue biopsy sampling device for bone in humans or animals, comprising:

a tube shaped casing or sleeve having a distal end provided with a cutting edge, and having a proximal end;

a needle for inserting in the sleeves, the needle extending out of the distal end of the sleeve when inserted in the sleeve, and having a tip enabling penetration in the bone;

the sleeve in the vicinity of its distal end exhibiting a portion having reduced outer diameter, and an intermediate essentially ring shaped portion between the distal end and the portion having reduced diameter;

the distal end having a section with continuously reducing inner diameter, over at least the major part of the section; and wherein the cutting edge having an ellipsoid circumference, and in side projection forms an angle in relation to a perpendicular plane through the cross section of the device, the angle being 5°–45°.

20. The sleeve as claimed in claim 19, wherein the angle preferably is 17°–23°.

* * * * *

UNITED STATES PATENT AND TRADEMARK OFFICE
CERTIFICATE OF CORRECTION

PATENT NO.   : 5,868,684
DATED        : February 9, 1999
INVENTOR(S)  : Dan Akerfeldt et al.

It is certified that error appears in the above-identified patent and that said Letters Patent is hereby corrected as shown below:

<u>Claim 15,</u>
Line 1, delete "device" and insert -- sleeve --.

<u>Claim 16,</u>
Line 1, delete "device" and insert -- sleeve --.

<u>Claim 17,</u>
Line 1, delete "8" and insert -- 10 --.

<u>Claim 20,</u>
Line 1, delete "sleeve" and insert -- device --.

Signed and Sealed this

Fourth Day of September, 2001

*Attest:*

*Attesting Officer*

NICHOLAS P. GODICI
*Acting Director of the United States Patent and Trademark Office*